United States Patent
Kim

(10) Patent No.: US 9,683,859 B2
(45) Date of Patent: Jun. 20, 2017

(54) METHOD FOR PROVIDING NAVIGATION USING WEARABLE DEVICE AND VEHICLE FOR CARRYING OUT THE SAME

(71) Applicant: HYUNDAI MOTOR COMPANY, Seoul (KR)

(72) Inventor: Dong Uk Kim, Incheon (KR)

(73) Assignee: HYUNDAI MOTOR COMPANY, Seoul (KR)

(*) Notice: Subject to any disclaimer, the term of this patent is extended or adjusted under 35 U.S.C. 154(b) by 0 days.

(21) Appl. No.: 14/746,827

(22) Filed: Jun. 22, 2015

(65) Prior Publication Data

US 2016/0209223 A1 Jul. 21, 2016

(30) Foreign Application Priority Data

Jan. 16, 2015 (KR) .................. 10-2015-0008196

(51) Int. Cl.
| | |
|---|---|
| *G01C 21/00* | (2006.01) |
| *G01C 21/34* | (2006.01) |
| *A61B 5/18* | (2006.01) |
| *G01C 21/36* | (2006.01) |
| *A61B 5/0205* | (2006.01) |
| *A61B 5/00* | (2006.01) |

(52) U.S. Cl.
CPC ............ *G01C 21/3423* (2013.01); *A61B 5/18* (2013.01); *A61B 5/681* (2013.01); *G01C 21/365* (2013.01); *G01C 21/3688* (2013.01); *A61B 5/02055* (2013.01); *A61B 5/4866* (2013.01)

(58) Field of Classification Search
CPC ............ G01C 21/3697; G01C 21/3679; G01C 21/3614; G01C 21/005

USPC ......... 701/36, 400, 416, 428, 433, 537, 533, 701/484, 538, 539; 340/988
See application file for complete search history.

(56) References Cited

U.S. PATENT DOCUMENTS

| | | | |
|---|---|---|---|
| 8,515,668 B2 | 8/2013 | Bruelle-Drews | |
| 2001/0025222 A1* | 9/2001 | Bechtolsheim .... | G01C 21/3423 701/410 |
| 2013/0054090 A1* | 2/2013 | Shin ....................... | B60K 28/06 701/36 |

(Continued)

FOREIGN PATENT DOCUMENTS

| | | | |
|---|---|---|---|
| JP | 2001-148092 A | 5/2001 | |
| JP | 2002-257579 A | 9/2002 | |

(Continued)

OTHER PUBLICATIONS

Korean Office Action dated Jun. 1, 2016 issued in Korean Patent Application No. 10-2015-0008196.

*Primary Examiner* — Gertrude Arthur Jeanglaud

(74) *Attorney, Agent, or Firm* — McDermott Will & Emery LLP

(57) ABSTRACT

A method for providing navigation using a wearable device by a vehicle includes performing wireless connection with the wearable device, receiving monitoring information regarding a driver from the connected wearable device, and determining, after setting of a destination, a walking course and a vehicle traveling course to the set destination in consideration of the monitoring information. Navigation for the walking course is provided by the wearable device and navigation for the vehicle traveling course is provided by a head unit of the vehicle.

20 Claims, 5 Drawing Sheets

(56) References Cited

U.S. PATENT DOCUMENTS

| | | | |
|---|---|---|---|
| 2014/0306833 A1* | 10/2014 | Ricci | ................... H04W 48/04 340/901 |
| 2014/0309864 A1* | 10/2014 | Ricci | ................... H04W 48/04 701/36 |
| 2015/0006077 A1* | 1/2015 | Baid | ................. G01C 21/3697 701/533 |

FOREIGN PATENT DOCUMENTS

| | | |
|---|---|---|
| JP | 2003-240588 A | 8/2003 |
| JP | 2004-301547 A | 10/2004 |
| JP | 2004-361325 A | 12/2004 |
| JP | 2006-029863 A | 2/2006 |
| JP | 2006-250879 A | 9/2006 |
| JP | 2011-122954 A | 6/2011 |
| JP | 2013-050353 A | 3/2013 |
| JP | 2013-134184 A | 7/2013 |
| JP | 2014-235078 A | 12/2014 |
| KR | 10-2013-0023478 A | 3/2013 |
| KR | 10-2014-0145332 A | 12/2014 |

\* cited by examiner

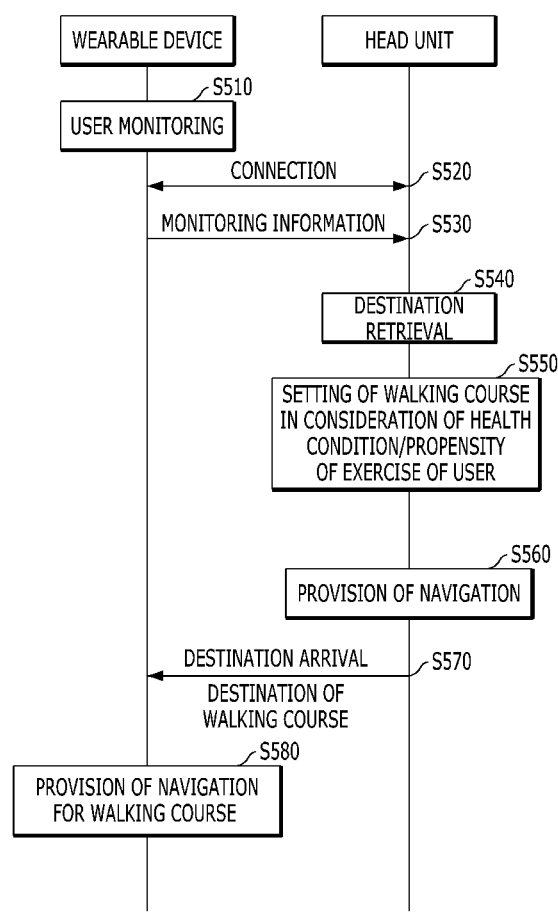

METHOD FOR PROVIDING NAVIGATION USING WEARABLE DEVICE AND VEHICLE FOR CARRYING OUT THE SAME

CROSS-REFERENCE TO RELATED APPLICATION

This application claims the benefit of Korean Patent Application No. 10-2015-0008196, filed on Jan. 16, 2015 with the Korean Intellectual Property Office, the disclosure of which is hereby incorporated by reference as if fully set forth herein.

BACKGROUND OF THE INVENTION

Field of the Invention

The present invention relates to a method capable of performing navigation via combination of walking and vehicle traveling using a wearable device and a vehicle capable of carrying out the same.

Discussion of the Related Art

Conventional navigation systems are divided into navigation systems for walking and navigation systems for vehicle traveling. Therefore, when a user attempts to travel a partial course to a specific destination using a vehicle and to travel the remaining course by walking, the user has to set the destination respectively in the above two types of navigation systems.

That is, a driver first has to get out of a vehicle and thereafter has to additionally set a walking destination, which causes difficulty in systematic management of a destination time. In addition, the propensity or desire of exercise and the body state of the driver are not completely taken into account in the setting of a walking destination.

SUMMARY OF THE INVENTION

Accordingly, the present invention is directed to a method for providing navigation using a wearable device and a vehicle for carrying out the same that substantially obviate one or more problems due to limitations and disadvantages of the related art.

An object of the present invention is to provide a convenient navigation method capable of combining a vehicle traveling course and a walking course with each other via a single destination retrieval for provision of navigation.

In particular, another object of the present invention is to provide a navigation method capable of setting a walking course in consideration of health conditions and the propensity of exercise of a user.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, a method for providing navigation using a wearable device by a vehicle may include performing wireless connection with the wearable device, receiving monitoring information regarding a driver from the connected wearable device, and determining, after setting of a destination, a walking course and a vehicle traveling course to the set destination in consideration of the monitoring information. Navigation for the walking course may be provided by the wearable device and navigation for the vehicle traveling course may be provided by a head unit of the vehicle.

In accordance with another aspect of the present invention, a head unit of a vehicle for providing navigation using a wearable device, may include a wireless communication unit configured to exchange data with the wearable device in a wireless manner, an output unit configured to output audio-visual information required to provide navigation, and a controller configured to receive monitoring information regarding a driver from the connected wearable device and to determine, after setting of a destination, a walking course and a vehicle traveling course to the set destination in consideration of the monitoring information. Navigation for the walking course may be provided by the wearable device and navigation for the vehicle traveling course may be provided by the output unit.

In accordance with another aspect of the present invention, a control method of a wearable device for providing navigation along with a head unit of a vehicle may include acquiring monitoring information related to a driver, performing wireless connection with the head unit of the vehicle, and determining, after setting of a destination, a walking course and a vehicle traveling course to the set destination in consideration of the monitoring information. Navigation for the walking course may be provided by the wearable device and navigation for the vehicle traveling course may be provided by the head unit of the vehicle.

In accordance with a further aspect of the present invention, a wearable device to provide navigation, along with a head unit of a vehicle may include a vital signal sensor configured to acquire monitoring information related to a driver, an output unit configured to output audio-visual information required to provide walking navigation, a wireless communication unit configured to exchange data with the head unit in a wireless manner, and a controller configured to determine, after setting of a destination, a walking course and a vehicle traveling course to the set destination in consideration of the monitoring information. Navigation for the walking course may be provided by the output unit and navigation for the vehicle traveling course may be provided by the head unit.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings:

FIG. 5 is a flowchart view illustrating another exemplary process of providing navigation according to an embodiment of the present invention.

DETAILED DESCRIPTION OF THE INVENTION

Figure 1:
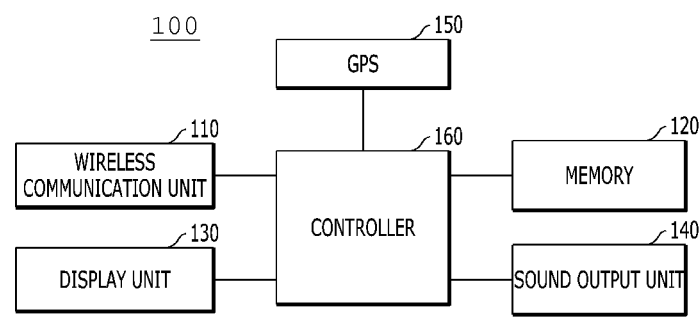
FIG. 1 is a block diagram illustrating an exemplary configuration of a head unit of a vehicle according to an embodiment of the present invention.

Hereinafter, reference will now be made in detail to the preferred embodiments of the present invention, examples of which are illustrated in the accompanying drawings. In the drawings, the same or similar elements are denoted by the same reference numerals even though they are depicted in different drawings, and a detailed description of the same or similar elements will be omitted. The suffixes "module" and "unit" of elements herein are used for convenience of description and thus can be used interchangeably and do not have any distinguishable meanings or functions.

In addition, in the following description of the embodiments disclosed herein, a detailed description of related known technologies will be omitted when it may make the subject matter of the embodiments disclosed herein rather unclear. In addition, the accompanying drawings have been made only for a better understanding of the embodiments disclosed herein and are not intended to limit technical ideas disclosed herein, and it should be understood that the accompanying drawings are intended to encompass all modifications, equivalents and substitutions included in the sprit and scope of the present invention.

Proposed in the present invention is that, in a case in which a passenger of a vehicle wears a wearable device, to provide navigation to a destination, a path to the destination is divided into a walking course and a vehicle traveling course such that navigation for the vehicle traveling course is provided via a head unit of a vehicle and navigation for the walking course is provided via the wearable device. At this time, division of the walking course and the vehicle traveling course may be performed by the wearable device and may be performed by the head unit of the vehicle. In addition, bio-information of a driver acquired by the wearable device and monitoring information such as previously input profiles may be referenced upon division of the respective courses. For example, the bio-information may include an average step speed and health conditions (e.g., a heart rate and fatigue degree), and the profiles may include, for example, a desired exercise distance/calorie burn and preference for uphill road/stairs.

First, a description will be given of the configuration of an apparatus for carrying out the embodiments of the present invention.

FIG. 1 is a block diagram illustrating an exemplary configuration of a head unit of a vehicle according to an embodiment of the present invention.

Referring to FIG. 1, the head unit, designated by reference numeral 100, of the vehicle may include a wireless communication unit 110 connected to a wearable device such as smart glasses or a bracelet/watch type wearable device via wireless communication protocols such as, for example, Bluetooth or Wi-Fi, to exchange data including an audio-visual signal with the wearable device, a memory 120 storing map/destination data, a display unit 130 to visually output a map and navigation-related information, a sound output unit 140 to output a guide sound upon execution of a navigation function, a GPS module 150 to acquire current location information, and a controller 160 to control the above-described components. The controller 160 may perform judgment and calculation required to carry out the present embodiment. For example, the controller 160 may control the overall process of establishing a wireless data path with the wearable device. The controller 160 may judge an optimum path to a destination upon receiving destination information from the connected wearable device and control the display unit 130 and the sound output unit 140 to output travel information for the judged path. In addition, upon reception of monitoring information from the wearable device, the controller 160 may set a walking course and a vehicle traveling course to the final destination using the received monitoring information.

Meanwhile, the display unit 130 and the sound output unit 140 may be called an output unit for convenience.

Figure 2:
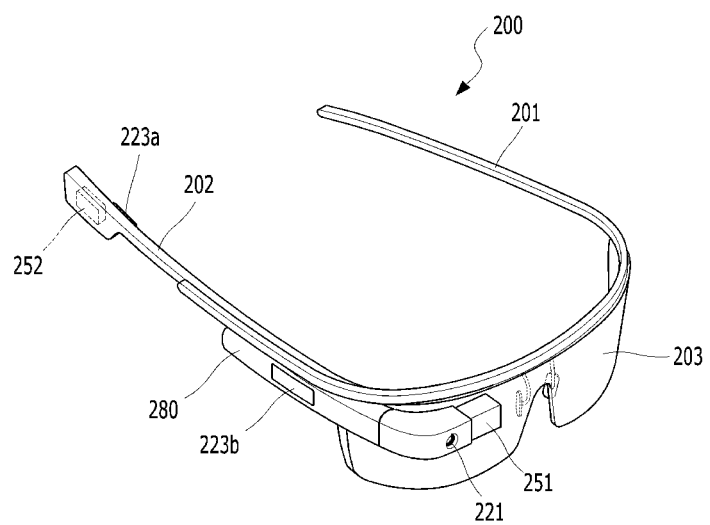
FIG. 2 is a view illustrating an example of smart glasses applicable to embodiments of the present invention.

FIG. 2 is a view illustrating an example of smart glasses applicable to embodiments of the present invention.

The smart glasses 200 are configured to be worn on the human head. To this end, the smart glasses 200 may include a frame unit (e.g., a case or housing). The frame unit may be formed of a flexible material for easy wearing. FIG. 2 illustrates the frame unit as including a first frame 201 and a second frame 202 formed of different materials.

The frame unit is supported by the head and internally defines a space for installation of various components. As illustrated, electronic components such as, for example, a control module 280 and a sound output module 252 may be mounted to the frame unit. In addition, a lens 203 to cover at least one of the left eye and the right eye may be separably coupled to the frame unit.

A display unit 251 may take the form of a head mounted display (HMD). The HMD is a display that is worn on the head of a user to display an image immediately in front of the user's eyes. To provide an image immediately in front of the user's eyes when the user wears the smart glasses 200, the display unit 251 may be located to correspond to at least one of the left eye and the right eye. FIG. 2 illustrates the display unit 251 as being located to correspond to the right eye so as to output an image toward the right eye of the user.

The display unit 251 may project an image to the user's eye using a prism. In addition, the prism may be a transparent to allow the user to view both the projected image and a general forward visual range (i.e. a viewing range through the user's eyes).

As described above, the image output through the display unit 251 may overlap a general driver's field of vision. Accordingly, the smart glasses 200 may provide navigation for a walking course based on augmented reality (AR).

A camera 221 is located proximate to at least one of the left eye and the right eye to capture a forward image. The camera 221 located proximate to the eye may acquire an image of a scene that the user views.

Although FIG. 2 illustrates the camera 221 as being incorporated in the control module 280, the position of the camera 221 is not limited thereto. The camera 221 may be installed to the frame unit and a plurality of cameras may be used to acquire a stereoscopic image.

The smart glasses 200 may include command input units 223a and 223b operated to receive a control command. The command input units 223a and 223b may be operated by touch or push action, for example.

The control module 280 is configured to control a variety of electronic components mounted to the smart glasses 200. For example, the control module 280 may allow establishment of a wireless data path with the head unit of the vehicle through a wireless communication unit (not shown) of the smart glasses 200, and transmit destination information or monitoring information through the established data path. In addition, upon reception of destination information from a smartphone, the control module 280 may set a walking course and a vehicle traveling course using the monitoring information and allow destination information of the set vehicle traveling course to be transmitted to the head unit of the vehicle. In addition, the control module 280 may control the sound output unit 252 and the display unit 251 to provide navigation for the walking course.

Meanwhile, vital signal sensors to monitor bio-information such as, for example, a body temperature and pulse, may be arranged at an inner surface of a distal end of the frame unit (i.e. legs of the glasses) coming into contact with the skin.

Although FIG. 2 illustrates the control module 280 as being installed to one side of the frame unit around the head, the position of the control module 280 is not limited thereto.

Figure 3:
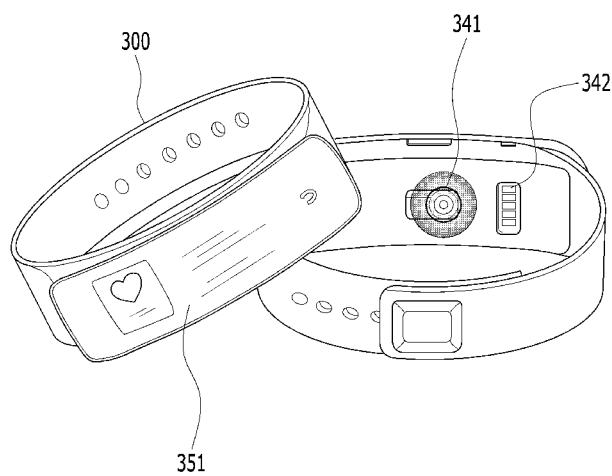
FIG. 3 is a view illustrating a bracelet/watch type wearable device applicable to embodiments of the present invention.

FIG. 3 is a view illustrating a bracelet/watch type wearable device applicable to embodiments of the present invention.

Referring to FIG. 3, the bracelet/watch type wearable device 300 may include vital signal sensors 341 and 342 affixed to an inner surface of a main body of the wearable device 300 coming into contact with the skin of a user, the vital signal sensor 341 being used to measure the body temperature and electrocardiogram (ECG) and the vital signal sensor 342 including an electrode for measurement of, for example, skin conductivity and electromyogram (EMG). In addition, a display unit 351 may be affixed to an outer surface of the main body to visually output the operational state of the wearable device 300, information acquired via the vital signal sensors 341 and 342, or navigation-related path information. Of course, the bracelet/watch type wearable device 300 may include, for example, a controller to control the aforementioned components and a wireless communication unit to exchange data with the head unit of the vehicle or a smartphone in a wireless manner, both the controller and the wireless communication unit being mounted in the main body.

A description will be given below of provision of a navigation function via interworking between the above-described head unit and a wearable device with reference to FIGS. 4 and 5.

Figure 4:
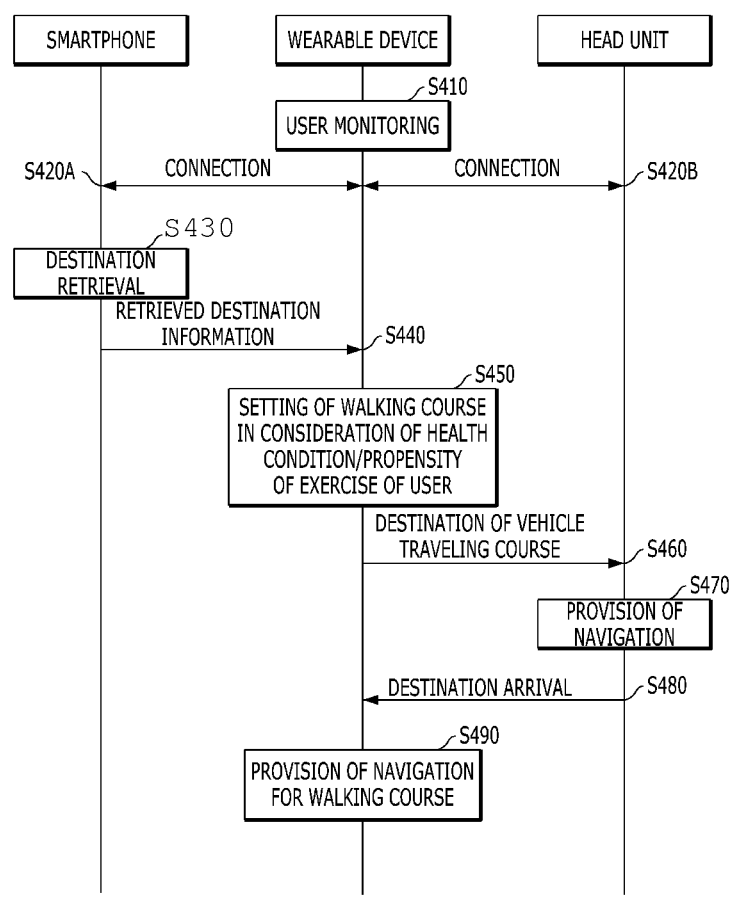
FIG. 4 is a flowchart illustrating an exemplary process of providing navigation according to an embodiment of the present invention.

FIG. 4 is a flowchart illustrating an exemplary process of providing navigation according to an embodiment of the present invention.

Referring to FIG. 4, a wearable device monitors the heath condition of the user periodically or based on an event (S410).

A smartphone may be wirelessly connected to the wearable device (S420A), and the wearable device may be wirelessly connected to the head unit of the vehicle (S420B).

When connection between the respective devices is completed, the user can retrieve a destination using the smartphone (S430). Destination retrieval using the smart phone is more convenient than that using the wearable device because the smartphone generally has a relatively large command input means such as, for example, a display unit and a touchscreen, which provides easier operation of the user. However, it is clear to those skilled in the art that this destination retrieval is given by way of example and destination retrieval may be performed using the wearable device.

When the destination is determined, retrieved destination information is transmitted to the wearable device (S440).

The wearable device sets a vehicle traveling course and a walking course using the transmitted destination information and monitoring information (i.e. profile information including, for example, the health condition and the propensity of exercise of the user)(S450). For example, when the user desires exercise and prefers stairs, the vehicle traveling course may be set to a short distance and the walking course may be set to include an uphill road or stairs. Even if the user desires exercise, the walking course may be set to a shorter distance (i.e. the vehicle traveling course may be set to a longer distance) upon determining that the user has a poor health condition at present.

After completion of the course setting, the wearable device transmits a location where the walking course begins, i.e. a destination of the vehicle traveling course to the head unit of the vehicle (S460).

The head unit of the vehicle provides a navigation function to the transmitted destination (S470). Then, when the vehicle reaches the destination, the head unit of the vehicle notifies the wearable device thereof (S480).

As a result, the wearable device provides navigation for the walking course to the final destination retrieved using the smartphone (S490).

The embodiment of FIG. 4 has been described as the final destination being retrieved using the smartphone and the wearable device setting the vehicle traveling course and the walking course. However, final destination retrieval and course setting may be performed by the head unit of the vehicle. This will be described below with reference to FIG. 5.

FIG. 5 is a flowchart view illustrating another exemplary process of providing navigation according to an embodiment of the present invention.

Referring to FIG. 5, a wearable device monitors the heath condition of the user periodically or based on an event (S510).

When the wearable device is wirelessly connected to the head unit (S520), the wearable device transmits acquired monitoring information to the head unit (S530).

When a destination is retrieved using the head unit (S540), the head unit sets a vehicle traveling course and a walking course using the received monitoring information (S550).

Thereafter, the head unit provides navigation to a beginning location of the set walking course (S560). Then, when the vehicle reaches the destination, the head unit of the vehicle notifies the wearable device thereof simultaneously with transmission of walking course destination information (i.e. information related to the retrieved final destination) (S570).

The wearable device may provide walking navigation to the corresponding destination upon receiving the walking course destination information (S580).

As is apparent from the above description, the following effects are acquired according to at least one embodiment of the present invention.

Upon provision of navigation to a destination, a walking course may be set in consideration of, for example, the propensity of exercise, health condition, and stamina of a person.

In addition, both a vehicle traveling course and a walking course may be conveniently set via single retrieval, and the accuracy of an estimated arrival time may be enhanced.

It will be appreciated by persons skilled in the art that the effects that can be achieved through the present invention are not limited to what has been particularly described hereinabove and other advantages of the present invention will be more clearly understood from the above detailed description.

The present invention as described above may be implemented as a computer readable code of a computer readable medium in which programs are recorded. The computer readable medium includes all kinds of recording devices in which data that may be read by a computer system is stored. Examples of the computer readable medium may include a hard disk drive (HDD), a solid state disk (SSD), a silicon disk drive (SDD), ROM, a RAM, a CD-ROM, a magnetic tape, a floppy disk, and an optical data storage device. In addition, the computer readable recording medium includes a carrier wave (e.g., data transmission over the Internet).

Accordingly, the above detailed description is not intended to be construed to limit the present invention in all aspects and be considered by way of example. The scope of the present invention should be determined by reasonable interpretation of the accompanying claims and all equivalent modifications made without departing from the present invention should be included in the following claims.

What is claimed is:

1. A method for providing navigation for a vehicle, the method comprising:
   establishing wireless connection with a wearable device;
   receiving health monitoring information regarding a driver from the connected wearable device;
   determining, after setting of a final destination, a first travel distance corresponding to a vehicle traveling course and a second travel distance corresponding to a walking course in consideration of the health monitoring information, navigation for the walking course provided by the wearable device and navigation for the vehicle traveling course provided by a head unit of the vehicle; and
   determining a vehicle traveling course destination based on the determined first travel distance,
   wherein both of the first travel distance and the second travel distance are determined before the navigation for the vehicle traveling course is provided by the head unit of the vehicle.

2. The method according to claim 1, further comprising:
   outputting navigation information during the vehicle traveling course; and
   transmitting information on the set final destination to the wearable device to allow the wearable device to provide the navigation for the walking course when the vehicle traveling course ends.

3. The method according to claim 1, wherein the health monitoring information includes health condition information and profile information of the driver.

4. The method according to claim 3, wherein the health condition information includes at least one of heart rate information, body temperature information, and fatigue degree information of the driver.

5. The method according to claim 3, wherein the profile information includes at least one of favorable path information, desired exercise distance information, and desired calorie burn information of the driver.

6. A head unit of a vehicle for providing navigation, the head unit comprising:
   a wireless communication unit configured to exchange data with a wearable device in a wireless manner;
   an output unit configured to output audio-visual information required to provide navigation; and
   a controller configured to receive health monitoring information regarding a driver from the connected wearable device, to determine, after setting of a final destination, a first travel distance corresponding to a vehicle traveling course and a second travel distance corresponding to a walking course in consideration of the health monitoring information, navigation for the walking course provided by the wearable device and navigation for the vehicle traveling course provided by the output unit, and to determine a vehicle traveling course destination based on the determined first travel distance,
   wherein both of the first travel distance and the second travel distance are determined before the navigation for the vehicle traveling course is provided by the head unit of the vehicle.

7. The head unit according to claim 6, wherein the controller is configured to control the output unit to provide the navigation during the vehicle traveling course, and to control the wireless communication unit to transmit information related to the set final destination to the wearable device so as to allow the wearable device to provide the navigation for the walking course when the vehicle traveling course ends.

8. The head unit according to claim 6, wherein the health monitoring information includes health condition information and profile information of the driver.

9. The head unit according to claim 8, wherein the health condition information includes at least one of heart rate information, body temperature information, and fatigue degree information of the driver.

10. The head unit according to claim 8, wherein the profile information includes at least one of favorable path information, desired exercise distance information, and desired calorie burn information of the driver.

11. A control method of a wearable device for providing navigation, the control method comprising:
    acquiring health monitoring information related to a driver;
    establishing wireless connection with a head unit of a vehicle;
    determining, after setting a final destination, a first travel distance corresponding to a vehicle traveling course and a second travel distance corresponding to a walking course in consideration of the health monitoring information, navigation for the walking course provided by the wearable device and navigation for the vehicle traveling course provided by the head unit of the vehicle; and
    determining a vehicle traveling course destination based on the determined first travel distance,
    wherein both of the first travel distance and the second travel distance are determined before the navigation for the vehicle traveling course is provided by the head unit of the vehicle.

12. The control method according to claim 11, further comprising:
    transmitting destination information of the vehicle traveling course to the head unit; and
    providing walking navigation to the set final destination when the head unit notifies the wearable device of end of the vehicle traveling course.

13. The control method according to claim 11, wherein the set final destination is received from a mobile device connected to the wearable device.

14. The control method according to claim 11, wherein the health monitoring information includes health condition information and profile information of the driver.

15. The control method according to claim 14, wherein the health condition information includes at least one of heart rate information, body temperature information, and fatigue degree information of the driver, and wherein the profile information includes at least one of favorable path information, desired exercise distance information, and desired calorie burn information of the driver.

16. A wearable device for providing navigation, the wearable device comprising:
- a vital signal sensor configured to acquire health monitoring information related to a driver;
- an output unit configured to output audio-visual information required to provide walking navigation;
- a wireless communication unit configured to exchange data with a head unit of a vehicle in a wireless manner; and
- a controller configured to determine, after setting of a final destination, a first travel distance corresponding to a vehicle traveling course and a second travel distance corresponding to a walking course in consideration of the monitoring information, navigation for the walking course provided by the output unit and navigation for the vehicle traveling course provided by the head unit, and to determine a vehicle traveling course destination based on the determined first travel distance, wherein both of the first travel distance and the second travel distance are determined before the navigation for the vehicle traveling course is provided by the head unit of the vehicle.

17. The wearable device according to claim 16, wherein the controller is configured to transmit destination information of the vehicle traveling course to the head unit and to control the output unit to provide walking navigation to the set final destination when the head unit notifies the wearable device of end of the vehicle traveling course.

18. The wearable device according to claim 16, wherein the final destination is received from a mobile device connected to the wearable device.

19. The wearable device according to claim 16, wherein the health monitoring information includes at least one of heart rate information, body temperature information, and fatigue degree information of the driver.

20. The wearable device according to claim 19, wherein the health monitoring information includes at least one of favorable path information, desired exercise distance information, and desired calorie burn information of the driver.

* * * * *